US00PP20567P2

(12) United States Plant Patent
Verwer

(10) Patent No.: US PP20,567 P2
(45) Date of Patent: Dec. 15, 2009

(54) ***DAHLIA* PLANT NAMED 'HS PRINCESS'**

(50) Latin Name: *Dahlia hybrida*
Varietal Denomination: HS Princess

(75) Inventor: Aad W. M. Verwer, Lisse (NL)

(73) Assignee: Verwer Dahlias B.V., Lisse (NL)

( * ) Notice: Subject to any disclaimer, the term of this patent is extended or adjusted under 35 U.S.C. 154(b) by 0 days.

(21) Appl. No.: 12/229,601

(22) Filed: Aug. 25, 2008

(51) Int. Cl.
*A01H 5/00* (2006.01)

(52) U.S. Cl. ..... Plt./321
(58) Field of Classification Search ..... Plt./321
See application file for complete search history.

*Primary Examiner*—Susan B McCormick Ewoldt
(74) *Attorney, Agent, or Firm*—C. A. Whealy

(57) ABSTRACT

A new and distinct cultivar of *Dahlia* plant named 'HS Princess', characterized by its compact, upright, somewhat outwardly spreading and mounded plant habit; freely branching growth habit; dark-colored foliage; freely flowering habit; daisy-type inflorescence form; inflorescences with blush pink to white-colored ray florets; and good postproduction longevity and garden performance.

2 Drawing Sheets

Botanical designation: *Dahlia hybrida* .
Cultivar denomination: 'HS Princess'.

BACKGROUND OF THE INVENTION

The present invention relates to a new and distinct cultivar of *Dahlia* plant, botanically known as *Dahlia hybrida*, and hereinafter referred to by the name 'HS Princess'.

The new *Dahlia* plant is a product of a planned breeding program conducted by the Inventor in Lisse, The Netherlands. The objective of the breeding program is to create new compact container-type *Dahlia* cultivars that have a freely basal branching growth habit, early and freely flowering habit, daisy inflorescence form, attractive ray floret coloration, and good postproduction longevity and garden performance.

The new *Dahlia* plant originated from an open-pollination in Lisse, The Netherlands during the summer of 2002 of a proprietary seedling selection of *Dahlia hybrida* identified as code number VD-0-49, not patented, as the female, or seed, parent with an unidentified selection of *Dahlia hybrida*, as the male, or pollen, parent. The new *Dahlia* was discovered and selected by the Inventor as a single flowering plant within the progeny of the stated open-pollination in a controlled environment in Lisse, The Netherlands during the summer of 2003.

Asexual reproduction of the new *Dahlia* by cuttings since the spring of 2004 in a controlled environment in Lisse, The Netherlands, has shown that the unique features of this new *Dahlia* are stable and reproduced true to type in successive generations.

SUMMARY OF THE INVENTION

Plants of the new *Dahlia* have not been observed under all possible environmental conditions. The phenotype may vary somewhat with variations in environment such as temperature and light intensity, without, however, any variance in genotype.

The following traits have been repeatedly observed and are determined to be the unique characteristics of 'HS Princess'.

These characteristics in combination distinguish 'HS Princess' as a new and distinct cultivar of *Dahlia:*

1. Compact, upright, somewhat outwardly spreading and mounded plant habit.
2. Freely branching growth habit.
3. Dark-colored foliage.
4. Freely flowering habit.
5. Daisy-type inflorescence form.
6. Inflorescences with blush pink to white-colored ray florets.
7. Good postproduction longevity and garden performance.

Plants of the new *Dahlia* differ from plants of the female parent selection in the following characteristics:

1. Plants of the new *Dahlia* are more compact than plants of the female parent selection.
2. Plants of the new *Dahlia* have stronger stems than plants of the female parent selection.
3. Plants of the new *Dahlia* and the female parent selection differ in leaf coloration as plants of the female parent selection have bronze-colored leaves.

Plants of the new *Dahlia* can be compared to plants of *Dahlia hybrida* 'HS First Love', disclosed in U.S. Plant Pat. No. 16,984. In side-by-side comparisons conducted in Lisse, The Netherlands, plants of the new *Dahlia* differed from plants of 'HS First Love' in the following characteristics:

1. Plants of the new *Dahlia* were more freely branching than plants of 'HS First Love'.
2. Plants of the new *Dahlia* had thicker stems than plants of 'HS First Love'.
3. Plants of the new *Dahlia* had darker-colored leaves than plants of 'HS First Love'.
4. Plants of the new *Dahlia* had larger inflorescences than plants of 'HS First Love'.
5. Plants of the new *Dahlia* and 'HS First Love' differed in ray floret color as plants of 'HS First Love' had salmon pink and red bi-colored ray florets.

BRIEF DESCRIPTION OF THE PHOTOGRAPHS

The accompanying photographs illustrate the overall appearance of the new *Dahlia*. The photographs show the colors as true as it is reasonably possible to obtain in colored reproductions of this type. Colors in the photographs may differ slightly from the color values cited in the detailed botanical description which accurately describe the colors of the new *Dahlia*.

The photograph on the first sheet comprises a side perspective view of a typical flowering plant of 'HS Princess' grown in a container.

The photograph on the second sheet is a close-up view of typical inflorescences of 'HS Princess'.

DETAILED BOTANICAL DESCRIPTION

The aforementioned photographs and following observations and measurements describe plants grown in Lisse, The Netherlands during the summer and autumn in an outdoor nursery and under conditions and practices which approximate those generally used in commercial *Dahlia* production. During the production of the plants, day temperatures ranged from 10° C. to 25° C. and night temperatures ranged from 5° C. to 20° C. Plants were pinched one time three weeks after planting. Measurements and numerical values represent averages for typical flowering plants. Plants were three to four months from planting when the photographs and description were taken. In the following description, color references are made to The Royal Horticultural Society Colour Chart, 1995 Edition, except where general terms of ordinary dictionary significance are used.

Botanical classification: *Dahlia hybrida* 'HS Princess'.

Parentage:

*Female, or seed, parent.*—Proprietary seedling selection of *Dahlia hybrida* identified as code number VD-0-49, not patented.

*Male, or pollen, parent.*—Unidentified selection of *Dahlia hybrida*, not patented.

Propagation:

*Type.*—By cuttings.

*Time to initiate roots, summer.*—About five days at temperatures of about 22° C.

*Time to initiate roots, winter.*—About seven days at temperatures of about 22° C.

*Time to produce a rooted young plant, summer.*—About 17 days at temperatures of about 22° C.

*Time to produce a rooted young plant, winter.*—About 19 days at temperatures of about 22° C.

*Root description.*—Thin, fleshy; close to 157D in color. If tubers develop, they are corky in texture and close to 199D in color.

*Rooting habit.*—Moderate branching; moderately dense.

Plant description:

*Plant form/growth habit.*—Compact, upright to somewhat outwardly spreading; mounded plant form. Freely basal branching with about six primary lateral branches; dense and bushy plant habit. Inflorescences held above the foliage on strong peduncles. Vigorous growth habit.

*Plant height.*—About 55 cm.

*Plant diameter or spread.*—About 50 cm.

*Lateral branches.*—Length: About 30 cm. Diameter: About 8 mm. Internode length: About 5 cm. Aspect: Erect to about 20° from vertical. Strength: Strong. Texture: Smooth, glabrous. Color: Close to 137A heavily overlain with close to 187B.

Foliage description:

*Arrangement.*—Leaves opposite; leaves may be single or compound with three or five leaflets.

*Shape.*—Ovate.

*Apex.*—Aristulate.

*Base.*—Attenuate.

*Margin.*—Serrate and divided; sinuses divergent.

*Length.*—Single leaves: About 6 cm. Compound leaves with three leaflets: About 12 cm. Compound leaves with five leaflets: About 21 cm.

*Width.*—Single leaves: About 4 cm. Compound leaves with three leaflets: About 12 cm. Compound leaves with five leaflets: About 10 cm.

*Venation pattern.*—Pinnate, reticulate.

*Texture, upper and lower surfaces.*—Smooth, glabrous.

*Color.*—Developing leaves/leaflets, upper surface: Close to 137A overlain with close to 187B. Developing leaves/leaflets, lower surface: Close to 191A. Fully expanded leaves/leaflets, upper surface: Close to 139A overlain with close to 187A; venation, close to 187A.

Fully expanded leaves/leaflets, lower surface: Close to 191A; venation, close to 187B.

*Petiole length.*—Single leaves: About 2 cm. Compound leaves with three leaflets: About 3 cm. Compound leaves with five leaflets: About 5 cm.

*Petiole diameter.*—Single leaves: About 1 mm. Compound leaves with three leaflets: About 2 mm. Compound leaves with five leaflets: About 4 mm.

*Petiole texture, upper and lower surfaces.*—Smooth, glabrous.

*Petiole color, upper surface.*—Close to 187A.

*Petiole color, lower surface.*—Close to 187B.

Inflorescence description:

*Appearance.*—Rotate single inflorescence form with ray and disc florets. Inflorescences positioned above the foliage on strong peduncles. Inflorescences face upright to slightly outwardly. Freely flowering habit; about 45 to 50 inflorescences develop per plant.

*Fragrance.*—None detected.

*Time to flower.*—Plants flower continuously during the summer and autumn in The Netherlands.

*Post-production longevity.*—Inflorescences maintain good substance for about two weeks on the plant and for about four to five days as a cut flower; inflorescences persistent.

*Inflorescence bud.*—Height: About 1.1 cm. Diameter: About 1.8 cm. Shape: Oblate. Color: Close to 147A; towards base, close to 200D.

*Inflorescence size.*—Diameter: About 9 cm. Depth (height): About 2 cm. Disc diameter: About 2.1 cm. Receptacle height: About 1.1 cm. Receptacle diameter: About 1.6 cm.

*Ray florets.*—Length: About 4.1 cm. Width: About 2.5 cm. Shape: Ovate. Apex: Mucronate. Base: Attenuate. Aspect: Initially upright to roughly perpendicular to the peduncle. Texture, upper and lower surfaces: Smooth, glabrous; velvety. Number of ray florets per inflorescence: About eight arranged in a single whorl. Color: When opening, upper and lower surfaces: Close to 155B; venation, close to 61A. Fully opened, upper surface: Close to 155B; venation, close to 155B. Fully opened, lower surface: Close to 155B; venation, close to 61A.

*Disc florets.*—Shape: Tubular; apex dentate. Length: About 1.9 cm. Diameter: About 2 mm. Number of disc florets per inflorescence: About 140. Color, immature: Apex: Close to 166A. Mid-section: Close to 14A. Base: Close to 1C. Color, mature: Apex: Close to 17B. Mid-section: Close to 14A. Base: Close to 17B.

*Phyllaries.*—Quantity per inflorescence: About five or six arranged in a single whorl. Length: About 1.7 cm. Width: About 8 mm. Shape: Ovate. Apex: Acuminate. Base: Attenuate. Margin: Entire. Texture, upper and lower surfaces: Smooth, glabrous. Color, upper surface: Close to 200A. Color, lower surface: Close to 187A.

*Peduncles.*—Length: Terminal peduncle: About 30 cm. Fourth peduncle: About 20 cm. Seventh peduncle: About 8 cm. Diameter: About 5 mm. Strength: Strong. Aspect: Erect to about 20° from vertical. Texture: Smooth, glabrous. Color: Close to 187B.

*Reproductive organs.*—Androecium: Quantity per disc floret: Five. Filament length: About 7 mm. Filament color: Close to 1C. Anther shape: Lanceolate. Anther length: About 6 mm. Anther color: Close to 16B. Pollen amount: Moderate. Pollen color: Close to 17A. Gynoecium: Quantity per ray or disc floret: One. Pistil length: About 6 mm. Stigma shape: Lanceolate. Stigma color: Close to 12B. Style length: About 8 mm. Style color: Close to 150C. Ovary color: Close to 8A. Fruits: Quantity per inflorescence: About 80. Length: About 2.6 cm. Diameter: About 2.5 cm. Texture: Smooth, glabrous. Color: Close to 187B. Seeds: Quantity per fruit: One. Length: About 8 mm. Diameter: About 2 mm. Color: Close to 199A.

Disease/pest resistance: Plants of the new *Dahlia* have not been shown to be resistant to pathogens and pests common to *Dahlia*.

Garden performance: Plants of the new *Dahlia* have exhibited good tolerance to rain and wind and have been observed to tolerate temperatures from about 0° C. to about 45° C.

It is claimed:

1. A new and distinct *Dahlia* plant named 'HS Princess' as illustrated and described.

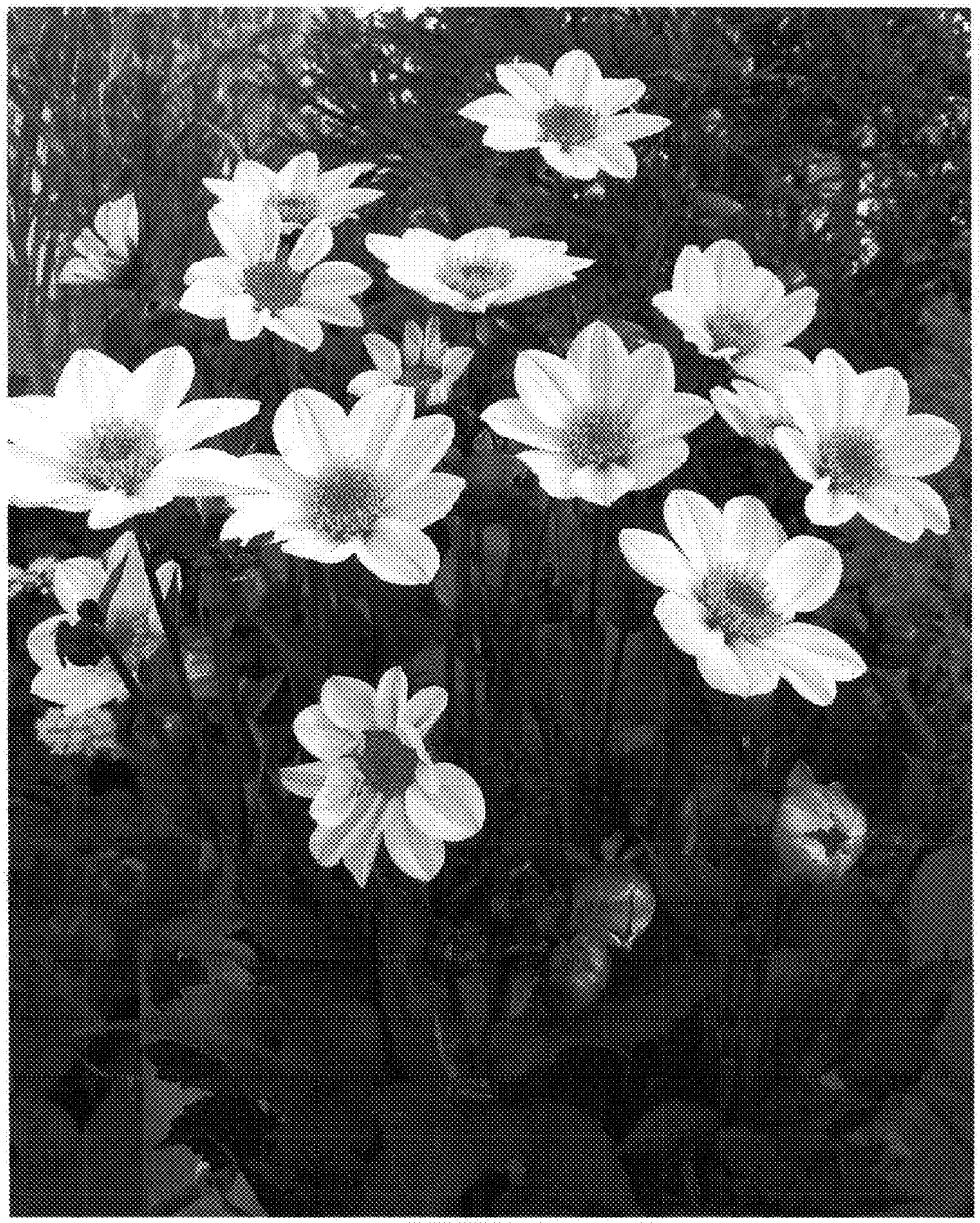

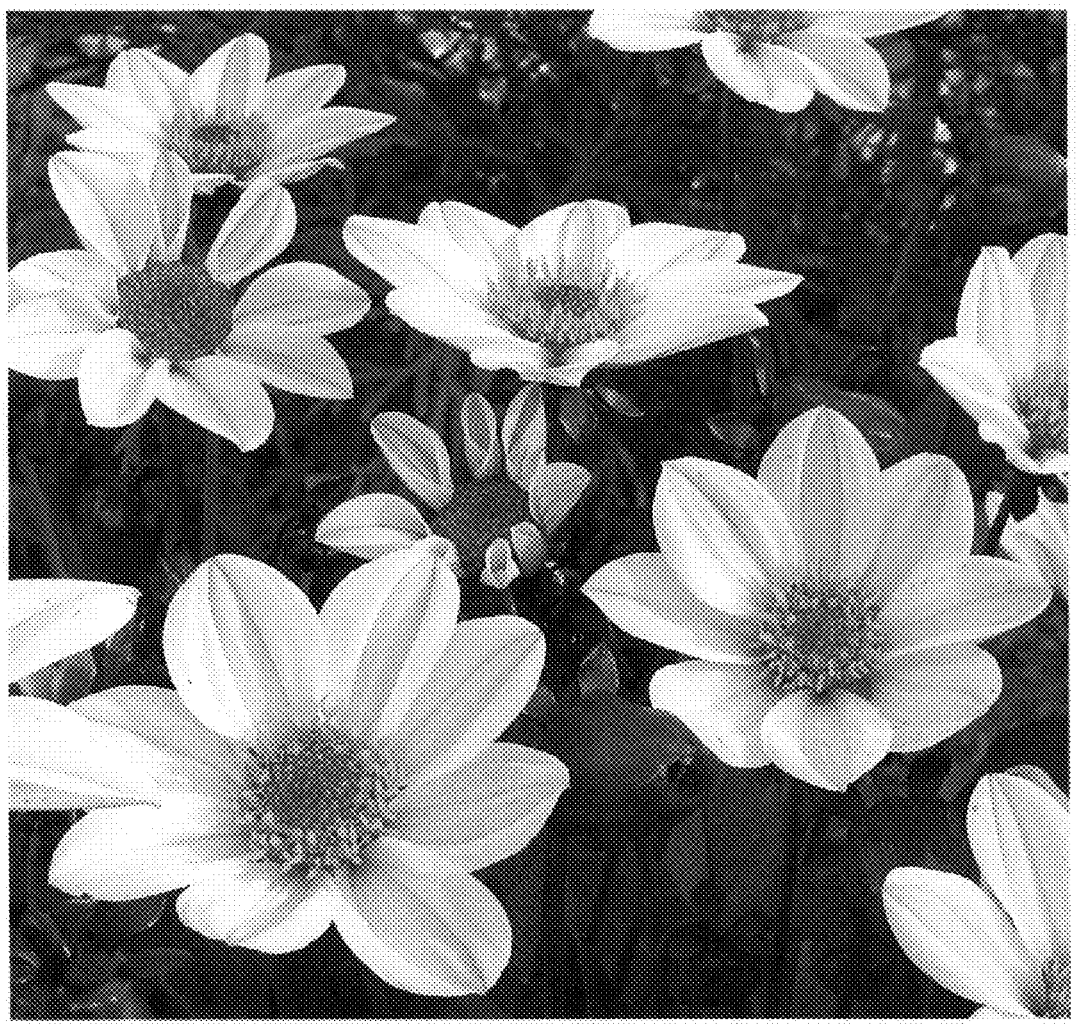

* * * * *